United States Patent [19]

Diethelm

[11] 4,273,783
[45] Jun. 16, 1981

[54] (1-ALKYL-5-NITRO-2-IMIDAZOLYL)-VINYL-GLYOXAL-DIACETALS, THEIR PREPARATION AND THEIR USE

[75] Inventor: Eugen Diethelm, Triesen, Liechtenstein

[73] Assignee: Grissman Chemicals Limited, England

[21] Appl. No.: 49,313

[22] Filed: Jun. 18, 1979

[30] Foreign Application Priority Data

Jun. 22, 1978 [GB] United Kingdom ............... 27635/78

[51] Int. Cl.³ .................. A61K 31/415; C07D 233/64
[52] U.S. Cl. .................................. 424/273 R; 548/339
[58] Field of Search ...................... 548/339; 424/273 R

[56] References Cited

U.S. PATENT DOCUMENTS 3,960,882  6/1976  Montanari ............................ 424/273

FOREIGN PATENT DOCUMENTS 4830059  9/1969  Japan ....................................... 548/339
4830060  9/1969  Japan ....................................... 548/339

*Primary Examiner*—Ethel G. Love
*Attorney, Agent, or Firm*—Ostrolenk, Faber, Gerb & Soffen

[57] ABSTRACT

(1-Alkyl-5-nitro-imidazolyl)-vinyl-glyoxal-diacetals of the formula:

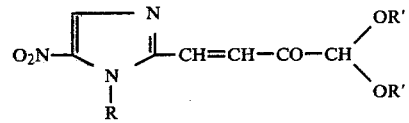

in which R and R' are each alkyl of 1 to 5 carbon atoms, are useful in the treatment of infections caused by protozoa, mycetes, and bacteria.

5 Claims, No Drawings

(1-ALKYL-5-NITRO-2-IMIDAZOLYL)-VINYL-GLYOXAL-DIACETALS, THEIR PREPARATION AND THEIR USE

DESCRIPTION

This invention relates to 5-nitro-imidazole derivatives having biological activity.

More particularly, this invention provides (1-alkyl-5-nitro-2-imidazolyl)-vinyl-glyoxal-diacetals of formula (I) below, having biological activity, and processes for their preparation. These new compounds are useful in therapy for treatment of patients suffering from infections caused by protozoa, mycetes, or bacteria.

This invention also provides pharmaceutical compositions containing, as a pharmacologically active component, a compound corresponding to the formula (I) below, and one or more of the usual extenders, additives, carriers and/or stabilisers.

It is known that vaginal infections, and, consequently those of the male partner, are of a mixed type, that is they are caused by a contemporaneous development of protozoa, mycetes and bacteria.

Unfortunately, as known to those skilled in the art, the pharmaceutical substances hitherto available are generally active either only on protozoa, or only on mycetes, or at last, only on bacteria. Thus, combatting said vaginal infections was particularly hard and required the contemporaneous administration of several drugs.

It has now been found that the compounds of this invention are anti-protozoal, antimycotic and antibacterial agents particularly effective in the therapeutic treatment of vulvovaginitis caused by *Trichomonas vaginalis*, of candidiasis caused by *Candida Albicans* and of bacterial infections caused by pathogenic microorganisms such as *Brucella bronchiseptica, Salmonella pullorum, Streptococcus pyogenes, Klebsiella pneunomoniae* and so on.

This is particularly important because, as before mentioned, being vaginal infections, and consequently the ones of the male partner, of mixed type, i.e. of protozoic-mycetic-bacteric type, it is possible, for the first time, to employ a single substance simultaneously active against the three classes of parasites.

It is further remarkable since really active antimycotic compounds are very few, and the 5-nitroimidazole derivatives of this invention are among the most active.

The fact of having at his own disposition agents which are active on pathogenic protozoa, mycetes and bacteria is of a great importance for the clinical physician, who does not to use several drugs and, meanwhile, is not in need of taking particular care, with the ensuing inconveniences and delays, in the diagnosis of the infection.

It is known that the diseases from *Tr.vaginalis* and *Candida Albicans* are very diffused among the female population, and that male is a fomes of infection, even though troubles caused by the infection are not apparent in himself.

Remarkable and determinant properties of the compounds of this invention are the very low toxicity and the fact that, when administered to pregnant women, they do not affect the regular development of foetus. Another favourable aspect provided by the compounds of the present invention is that they have no action on normal vaginal microflora, also including *Bacillus doderlein*.

The compounds of this invention also have a further very important property: they can be used both topically and per os.

The compounds of this invention are absorbed very little by the gastrointestinal tract, are quickly metabolised to inactive, fully atoxic compounds (and hence they do not provide summation); however, being very active even on *Amoeba-hystolitica*, they can be used also for treating this infection, which is very diffuse in tropical countries and is now treated by agents which are not free from remarkable side effects, also because of the high doses applied.

The compounds of this invention correspond to the general formula (I)

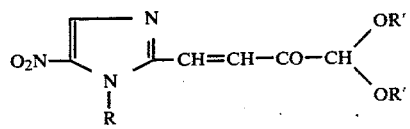

wherein R and R', which may be the same or different from each other, are either straight or branched chain alkyl groups of 1 to 5 carbon atoms.

The compounds of the present invention can be prepared in several ways, but the method preferred at present because of its simplicity, cheapness and the high yield of active product is the reaction of a 1-alkyl-5-nitro-2-formyl-imidazole of formula:

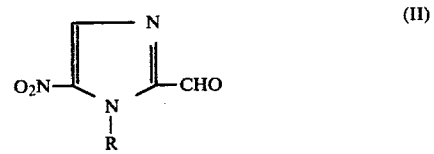

and a dialkyl-acetal of formula:

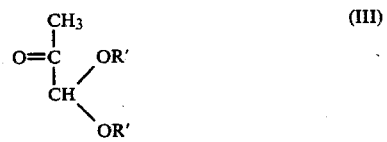

with resulting elimination of a water molecule.

In these formulae, R and R' have the meanings pointed out for the general formula (I).

It is surprising that the above reaction occurs very well in an aqueous medium, in neutral condition. For example, 1 mole of 1-methyl-5-nitro-2-formylimidazole is taken to the boiling temperature of water and 1 mole of pyruvaldehyde dimethylacetal is added slowly. At the end of the addition, still with the mixture at the boiling point, at first a fully clear, yellow solution occurs, and then the desired product, in flat, crystalline needles, is formed.

The 5-nitro-1-alkyl-2-formyl-imidazoles useful for preparing the compounds of this invention are described by Henry et al in the U.S. Pat. No. 3,472,864, where also several methods for the preparation thereof are referred to.

Another method for preparing the compounds of this invention at present preferred consists of reacting a 1-alkyl-5-nitro-imidazole with trioxymethylene and oxidising the resulting carbinol successively with manganese oxide.

Methylglyoxal dimethylacetal or pyruvaldehyde dimethylacetal are readily available on the market.

The compounds of the present invention can be administered to patients in the most suitable form, for example, either orally or topically, or in both ways. The ideal posology is, orally, 200 mg/day in capsules for 3-4 days either as a single or as two daily administration.

Topically, it is enough to apply a vaginal candle pro die, of 400 mg for 3-5 days.

Mixed administrations can be applied.

Capsules and candles are two of the pharmaceutical forms usable. However, the compounds of the present invention can be also used as a syrup or as tablets, orally, and as pure creams or spray for topical application.

Concurrence of mycotic and protozoal infections of the vagina varies from 5 to 14%. Concurrence of protozoal and bacterial infections is about 75%. Vaginal moniliasis concerns 14% of women who take the contraceptive pill and 22% of the pregnant ones.

The compounds of the present invention can be administered also in veterinary medicine.

In the following Examples, there is described only one of the many variants of the process which can be used for the synthesis of (1-alkyl-5-nitro-2-imidazolyl)-vinyl-glyoxal-diacetals according to this invention. However, it will be obvious to those skilled in the art, that the features of the process according to the invention can be widely changed in a general way, with regard to reaction conditions, and adapted to individual circumstances.

According to the character of the starting substance, it is not difficult for anyone who is skilled in the art to prepare the desired product.

EXAMPLE 1

15.5 g (0.1 mole) of 5-nitro-1-methyl-2-formylimidazole are added to 155 ml of water, in a vessel provided with a dropping funnel, a reflux condenser and a stirrer. The mixture is taken to light boiling and 22.8 g of pyruvaldehyde dimethylacetal are allowed to drop into the same in 15 minutes. It is left at light boiling for a further 15 minutes. The solution first becomes clear and yellow coloured, and a crystalline precipitate is then formed. It is left cooling at room temperature under stirring, and then it is filtered, and the residue is vacuum dried and crystallised from ethanol.

25-26 g of pure product are obtained which is a yield of 70% of the theoretical.

The structure, as verified by IR and NMR spectra, is that of 1-methyl-5-nitro-2-imidazolyl-vinyl-glyoxal-dimethylacetal. Melting point=112° C. Hereinafter, this compound will be referred to, in this Specification, as DP-1.

EXAMPLE 2

In vitro tests to measure the activity of DP-1 on *Trichomonas vaginalis* have been performed by using three strains of protozoon, therein referred to as A, B, and C. The medium for maintaining the strain is the one described in Proceedings of Society of Experimental Biological Medicine, Vol. 67, page 304.

The activity measured was 0.15 mcg/ml.

EXAMPLE 3

Activity on *Candida Albicans* of DP-1, measured by conventional methods, was found to be 1-2 mcg/ml, according to the strain applied.

DP-1 was assayed for anti-bacterial activity on several micro-organisms, as compared to metronidazole, and the results are given in the following Table:

| Micro-organism | Activity in mcg/ml | |
|---|---|---|
| | DP-1 | Metronidazole |
| Bacillus Subt. | <12.5 | >100 |
| Brucella Bronchiseptica | <12.5 | >100 |
| Salmonella pullorum | <12.5 | >100 |
| Streptococcus pyogenes | <12.5 | >100 |
| Klebsiella pneumoniae | <12.5 | >100 |

EXAMPLE 4

DP-1 was applied, clinically, to women suffering from trichomoniasis, at the dose of 200 mg/day for 3 days.

Full recovery, without relapses, occurred in 95% of the cases (20 patients).

In female patients suffering from monoliasis, the same recovery percentage occurred. The same results occurred with the application of vaginal candles.

I claim:

1. (1-Alkyl-5-nitro-imidazolyl)-vinyl-glyoxal-diacetal of the formula:

$$O_2N-\underset{\underset{R}{N}}{\overset{N}{\underset{\|}{\bigsqcup}}}-CH=CH-CO-CH\underset{OR'}{\overset{OR'}{\diagup}} \quad (I)$$

in which R and R', which may be the same or different, each represent straight or branched chain alkyl groups of 1 to 5 carbon atoms each.

2. 1-Methyl-5-nitro-2-imidazole-vinyl-glyoxal-dimethylacetal.

3. A method of treatment of infections caused by protozoa, mycetes, or bacteria in a host comprising the administration thereto of an anti-protozoal, anti-mycotic or anti-bacterial effective amount of a compound of formula (I) according to claim 1 or 2.

4. A pharmaceutical composition for the treatment of vulvaginitis comprising an anti-vulvaginitis effective amount of a compound of formula (I) according to claim 1 or 2, and one or more pharmaceutically acceptable extenders, additives, carriers and/or stabilizers.

5. A composition as claimed in claim 4 in the form of a tablet, capsule, syrup, spray, cream or vaginal candle.

* * * * *